United States Patent
Lin et al.

(10) Patent No.: US 6,589,481 B1
(45) Date of Patent: Jul. 8, 2003

(54) APPARATUS AND METHOD TO PRETREAT AND STERILIZE A LUMEN DEVICE

(75) Inventors: Szu-Min Lin, Laguna Hills, CA (US); Paul T. Jacobs, Trabuco Canyon, CA (US); Jenn-Hann Wang, Mission Viejo, CA (US); Alfredo M Choperena, San Juan Capistrano, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/222,966

(22) Filed: Dec. 30, 1998

Related U.S. Application Data

(63) Continuation-in-part of application No. 08/628,965, filed on Apr. 4, 1996.

(51) Int. Cl.[7] ............................... A61L 2/00; A61L 9/00
(52) U.S. Cl. ...................... 422/33; 422/20; 422/22; 422/28; 422/32; 422/292; 422/305
(58) Field of Search ................. 422/20, 22, 28, 422/292, 305, 306, 906, 944, 33, 32, 300

(56) References Cited

U.S. PATENT DOCUMENTS

| | | | |
|---|---|---|---|
| 4,169,123 A | | 9/1979 | Moore et al. .................. 422/29 |
| 4,169,124 A | | 9/1979 | Forstrom et al. ............. 422/33 |
| 4,230,663 A | | 10/1980 | Forstrom et al. ............. 422/33 |
| 4,337,223 A | * | 6/1982 | Kaye ......................... 422/112 |
| 4,410,492 A | * | 10/1983 | Kaye ........................... 422/27 |
| 4,643,876 A | | 2/1987 | Jacobs et al. .................. 422/23 |
| 4,756,882 A | | 7/1988 | Jacobs et al. .................. 422/23 |
| 4,909,999 A | | 3/1990 | Cummings et al. ......... 422/298 |
| 4,943,414 A | * | 7/1990 | Jacobs et al. .................. 422/28 |
| 4,952,370 A | | 8/1990 | Cummings et al. ........... 422/28 |
| 4,956,145 A | | 9/1990 | Cummings et al. ........... 422/28 |
| 5,087,418 A | * | 2/1992 | Jacob | |
| 5,115,166 A | * | 5/1992 | Campbell et al. | |
| 5,286,448 A | | 2/1994 | Childers ....................... 422/28 |
| 5,310,524 A | * | 5/1994 | Campbell et al. | |
| 5,346,075 A | | 9/1994 | Nichols et al. ............. 211/60.1 |
| 5,413,758 A | * | 5/1995 | Caputo et al. | |
| 5,413,760 A | | 5/1995 | Campbell, deceased et al. ............................ 422/24 |
| 5,425,815 A | * | 6/1995 | Parker et al. ................. 134/26 |
| 5,443,801 A | | 8/1995 | Langford ..................... 422/28 |
| 5,451,368 A | * | 9/1995 | Jacob | |
| 5,492,672 A | | 2/1996 | Childers et al. .............. 422/28 |
| 5,527,508 A | * | 6/1996 | Childers et al. | |
| 5,534,221 A | * | 7/1996 | Hillebrenner et al. | |

(List continued on next page.)

FOREIGN PATENT DOCUMENTS

| | | | | |
|---|---|---|---|---|
| CA | 214 9923 | | 6/1994 | |
| DE | 2623917 A1 | * | 12/1977 | ............ A61M/1/03 |
| DE | 41 02 055 A1 | * | 8/1991 | ............ A61L/2/20 |
| EP | 0 223 479 A2 | * | 5/1987 | ............ A61L/2/18 |
| EP | 0 302 419 B1 | * | 2/1989 | ............ A61L/2/20 |
| EP | 0 207 417 B1 | * | 9/1990 | ............ A61L/2/14 |
| EP | 0 456 135 A2 | * | 5/1991 | ............ A61L/2/14 |
| EP | 0 302 419 B1 | | 9/1992 | |

Primary Examiner—Robert J. Warden, Sr.
Assistant Examiner—Monzer R. Chorbaji
(74) Attorney, Agent, or Firm—Knobbe, Martens, Olson & Bear, LLP

(57) ABSTRACT

Various forms of apparatus and methods for pretreating and sterilizing a lumen with a peroxide solution prior to sterilization of the interior of the lumen by exposing the lumen to reduced pressure and, optionally, plasma in a sterilization chamber. The pretreatment is preferably done before placing the lumen in the sterilization chamber. The method also includes exposure of the exterior of the lumen to peroxide vapor to sterilize the exterior of the lumen. Pretreatment of the interior of the lumen with liquid peroxide greatly improves the efficiency of sterilization of the interior. Exposure of the lumen to plasma reduces the time required for sterilization.

29 Claims, 12 Drawing Sheets

U.S. PATENT DOCUMENTS

| | | | |
|---|---|---|---|
| 5,556,607 A | * | 9/1996 | Childers et al. |
| 5,558,841 A | | 9/1996 | Nakagawa et al. .......... 422/105 |
| 5,570,739 A | | 11/1996 | Krawchuk et al. ....... 548/335.5 |
| 5,580,530 A | | 12/1996 | Kowatsch et al. .......... 422/102 |
| 5,633,424 A | | 5/1997 | Graves et al. .............. 588/227 |
| 5,656,238 A | | 8/1997 | Spencer et al. ............... 422/23 |
| 5,667,753 A | | 9/1997 | Jacobs et al. ................. 422/29 |
| 5,674,450 A | * | 10/1997 | Lin et al. ...................... 422/29 |
| 5,714,119 A | * | 2/1998 | Kawagoe et al. ............. 422/21 |
| 5,792,422 A | | 8/1998 | Lin et al. ...................... 422/31 |
| 5,882,589 A | * | 3/1999 | Mariotti ....................... 422/28 |

\* cited by examiner

APPARATUS AND METHOD TO PRETREAT AND STERILIZE A LUMEN DEVICE

This application is a continuation-in-part of application Ser. No. 08/628,965, filed Apr. 4, 1996, hereby incorporated by reference in its entirety.

FIELD OF THE INVENTION

This invention relates to a method and apparatus for pretreating a lumen with a source of peroxide before sterilization at low pressure in a chamber.

BACKGROUND OF THE INVENTION

Medical instruments have traditionally been sterilized using either heat, such as is provided by steam, or a chemical, such as formaldehyde or ethylene oxide in the gas or vapor state. Each of these methods has drawbacks. Many medical devices, such as fiberoptic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long.

Sterilization using liquid hydrogen peroxide solution has been found to require a high concentration of sterilant, extended exposure times and/or elevated temperatures. However, sterilization using hydrogen peroxide vapor has been shown to have some advantages over other chemical sterilization processes (see, e.g., U.S. Pat. Nos. 4,169,123 and 4,169,124). The combination of hydrogen peroxide with a plasma provides certain additional advantages, as disclosed in U.S. Pat. No. 4,643,876, issued Feb. 17, 1987 to Jacobs et al. U.S. Pat. No. 4,756,882, issued Jul. 12, 1988, also to Jacobs et al. discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles, even within closed packages. Further, these methods of combining hydrogen peroxide vapor with a plasma, while useful in "open" systems, have been found to be inadequate to effect sterilization in articles having diffusion-restricted areas, since the methods are dependent upon diffusion of the sterilant vapor into close proximity with the article before sterilization can be achieved. Thus, these methods have been found to require high concentration of sterilant, extended exposure time and/or elevated temperatures when used on long, narrow lumens. For example, lumens longer than 27 cm and/or having an internal diameter of less than 0.3 cm have been particularly difficult to sterilize. Thus, no simple, safe, effective method of sterilizing smaller lumens exists in the prior art.

The sterilization of articles containing diffusion-restricted areas, such as long narrow lumens, therefore presents a special challenge. Methods that use hydrogen peroxide vapor that has been generated from an aqueous solution of hydrogen peroxide have certain disadvantages, because:

1. Water has a higher vapor pressure than hydrogen peroxide and will vaporize faster than hydrogen peroxide from an aqueous solution.

2. Water has a lower molecular weight than hydrogen peroxide and will diffuse faster than hydrogen peroxide in the vapor state.

Because of this, when an aqueous solution of hydrogen peroxide is vaporized in the area surrounding the items to be sterilized, the water reaches the items first and in higher concentration. The water vapor therefore becomes a barrier to the penetration of hydrogen peroxide vapor into diffusion restricted areas, such as small crevices and long narrow lumens. One cannot solve the problem by removing water from the aqueous solution and using more concentrated hydrogen peroxide, since, among other reasons, concentrated solutions of hydrogen peroxide greater than 65% by weight can be hazardous due to the oxidizing nature thereof.

U.S. Pat. No. 4,952,370 to Cummings et al. discloses a sterilization process wherein aqueous hydrogen.peroxide vapor is first condensed on the article to be sterilized, and then a source of vacuum is applied to the sterilization chamber to evaporate the water and hydrogen peroxide from the article. This method is suitable to sterilize surfaces, however, it is ineffective at rapidly sterilizing diffusion-restricted areas, such as those found in lumened devices, since it too depends on the diffusion of the hydrogen peroxide vapor into the lumen to effect sterilization.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized. Potentially, the area between the vessel and the lumen may be occluded from the sterilization process. In addition, water is vaporized faster and precedes the hydrogen peroxide vapor into the lumen.

In U.S. Patent. No. 5,492,672, there is disclosed a process for sterilizing narrow lumens. This process uses a multi-component sterilant vapor and requires successive alternating periods of flow of sterilant vapor and discontinuance of such flow. A complex apparatus is used to accomplish the method. Because flow through of vapor is used, closed end lumens are not readily sterilized in the process.

Thus, there remains a need for a simple and effective method of vapor sterilization of articles having areas where diffusion of these vapors is restricted, such as long, narrow lumens.

SUMMARY OF THE INVENTION

One aspect of the present invention relates to an apparatus for pretreating a lumen. The apparatus comprises a connector containing hydrogen peroxide, where the connector is attached to one end of the lumen, means for creating a pressure difference between the connector and the second end of the lumen, where the second end of the lumen is at a lower pressure than the connector, causing the hydrogen peroxide to flow through the lumen.

In one embodiment, the hydrogen peroxide is a liquid. Preferably, the apparatus also includes a receptacle containing a liquid comprising hydrogen peroxide, where the receptacle is attached to the connector. In another aspect, the connector is collapsible.

In another embodiment, the hydrogen peroxide is a mist or aerosol. Advantageously, the apparatus additionally comprises a generator of mist or aerosol, where the generator of mist or aerosol is attached to the connector in a manner allowing the mist or aerosol to enter the connector.

In one embodiment, the generator of mist or aerosol is a humidifier. Preferably, the humidifier comprises an ultrasonic transducer. In other embodiments, the generator of mist or aerosol comprises a liquid spray nozzle, a tank containing a liquid comprising hydrogen peroxide with a gas nozzle situated at least partially in the liquid, or a nebulizer.

Preferably, the means for creating the pressure difference between the connector and the second end of the lumen is a source of vacuum.

Advantageously, the apparatus for pretreating the lumen additionally comprises a vacuum chamber capable of vaporizing hydrogen peroxide and a source of sterilant located in an enclosure, where the enclosure is in fluid communication with the chamber and is able to introduce sterilant into the interior of the chamber. Preferably, the sterilant comprises hydrogen peroxide.

Advantageously, the apparatus additionally comprises a source of plasma. Preferably, the apparatus additionally comprises a heat source to heat the enclosure.

Another aspect of the invention is a method of pretreating and sterilizing the interior and exterior of a lumen comprising contacting the interior of the lumen with a liquid comprising hydrogen peroxide, where the liquid is delivered from a source of liquid, placing the lumen in a chamber, where the placing occurs before or after contacting, removing the source of liquid from the lumen, evacuating the chamber, where the source of liquid is removed before evacuating, introducing sterilant into the chamber from an enclosure in fluid communication with the chamber, vaporizing the liquid in the interior of the lumen, and sterilizing the interior and exterior of the lumen.

In a preferred embodiment, the contacting can occur via one or more of the following methods: direct delivery, injection, static soak, liquid flow-through, aerosol or mist, condensation, or physical placement.

Advantageously, the lumen is also exposed to a plasma. The plasma may be generated in the chamber with the lumen, or it may be generated in a second chamber and flowed into the chamber with the lumen. Preferably, the sterilant comprises hydrogen peroxide.

In one aspect of the invention the contacting of the interior of the lumen with the liquid comprising hydrogen peroxide comprises attaching a collapsible container containing a liquid comprising hydrogen peroxide to an end of the lumen, and generating a pressure difference between the collapsible container and the other end of the lumen, where the other end is at a lower pressure than the container, collapsing the collapsible container and contacting the liquid with the interior of the lumen.

In another aspect of the invention, the contacting with the interior of the lumen comprises attaching a container containing a liquid comprising hydrogen peroxide to an end of the lumen and generating a pressure difference between the container and the other end of the lumen, where the other end of the lumen is at a lower pressure than the container.

Alternatively, the contacting can occur by generating a mist or aerosol comprising hydrogen peroxide, flowing the mist or aerosol into a connector attached to a first end of the lumen, and generating a pressure difference between the connector and the other end of the lumen, where the other end of the lumen is at a lower pressure than the connector, thereby contacting the interior of the lumen with the mist or aerosol.

In another aspect of the invention, the sterilant is introduced into the chamber before or during the vaporization of the liquid in the lumen. Advantageously, the introducing the sterilant from the enclosure is a concentrating process. Preferably the sterilant is generated from a source of sterilant. Advantageously, the source of sterilant is a liquid peroxide or a solid peroxide complex. The source of sterilant may be introduced into the enclosure either before or during evacuation.

DETAILED DESCRIPTION OF THE PREFERRED EMBODIMENT

Figure 1:
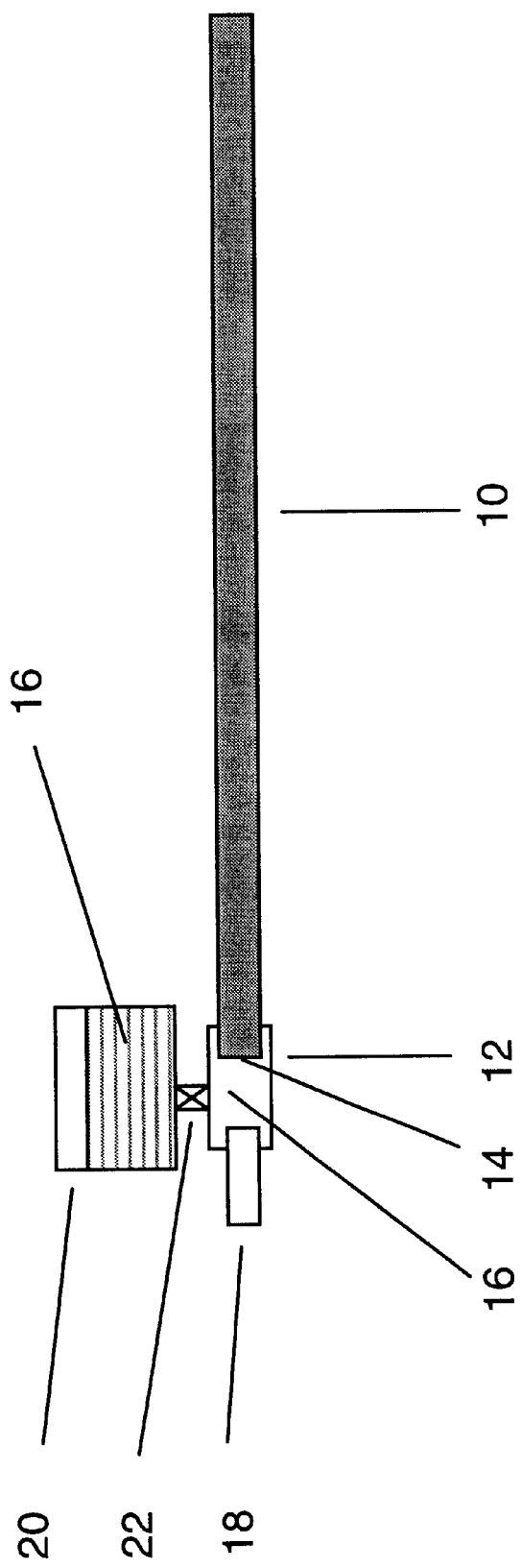
FIG. 1 is a side view of an apparatus for pretreating a lumen with a solution comprising hydrogen peroxide in which pressure pushes the solution from a connector into the interior of the lumen.

Sterilizing the inside of lumened devices has always posed a challenge to sterilization systems. Achieving rapid sterilization of lumened devices or other diffusion restricted articles at low temperatures and low concentrations of sterilant represents an even greater challenge. In the present invention, the shortcomings of the prior art sterilization systems are overcome by pre-treating or contacting articles to be sterilized with a source of peroxide prior to exposure to a reduced pressure sterilization process, or optionally, a reduced pressure sterilization process and a plasma. The source of peroxide comprises a liquid or condensed vapor. The liquid comprises aqueous solutions of hydrogen peroxide or peracetic acid or mixtures thereof. The vapor comprises hydrogen peroxide or peracetic acid vapor or mixtures thereof. The preferred method of the present invention utilizes aqueous hydrogen peroxide as the source of peroxide to contact an article to be sterilized. The methods of the present invention provide for the rapid sterilization of lumened and non-lumened articles under conditions that will not damage the articles nor leave toxic residues on the sterile articles.

In the method of the present invention, the source of the peroxide is delivered into direct contact with the article to be sterilized. In the case of a lumened device, the source of peroxide may be delivered directly into the lumen. In the case of an article having an area where diffusion of vapor is restricted, the source of peroxide may be delivered to the interior of the diffusion restricted area. For articles which are not diffusion-restricted, the source of peroxide can be introduced anywhere into the sterilizer. The source of peroxide is delivered into the lumen or into contact with the article to be sterilized or into contact with the sterilizer containing the article to be sterilized through means such as direct delivery or physical placement, a static soaking process, a liquid flow-through process, by mist or aerosol spray or by condensation of a vapor. Physical placement also includes placement of a reservoir containing the source of peroxide. In the preferred method of the present invention, the aqueous solutions of hydrogen peroxide can be relatively dilute, e.g., as low as 1–6% or lower by weight, since sterilization is not achieved through contact with the hydrogen peroxide solution, but rather, is achieved at low temperatures and in short periods of time upon exposure to hydrogen peroxide vapor under vacuum or vacuum combined with plasma. The method of the present invention is particularly effective with articles having inaccessible or hard-to-reach places. Such articles include long, narrow lumens, hinges, and other articles having spaces where diffusion of vapors is restricted.

The general operation of one embodiment of a preferred method of the present invention, which is useful for sterilizing the inside of long, narrow lumens, is as follows:

1. The interior of the lumen to be sterilized is contacted with a source of peroxide. The source of peroxide can be physically delivered as a small amount directly into the lumen, or by static soaking, liquid flow-through, mist or aerosol spray or condensation of a vapor.

2. The lumen to be sterilized is placed within a chamber, and the chamber is sealed and evacuated. (The source of peroxide can also be delivered to the inside of the lumen after placing the lumen in the chamber.)

3. The lumen is exposed to the vacuum for a period of time and at a temperature sufficient to effect sterilization.

4. The sterile lumen is removed from chamber.

The contacting of the interior of the lumen can be done inside or outside of the chamber. In general, contacting outside of the chamber is preferred.

An alternative embodiment of the present invention comprises an apparatus and method to pretreat the interior of a lumen in an article. In this embodiment, a source of peroxide is delivered into the lumen through means such as direct delivery, injection, physical placement, static soaking, liquid flow-through, by mist or aerosol spray, or by condensation of a vapor. Physical placement also includes placement of a reservoir containing the source of peroxide. The reservoir can be either rigid or flexible. Delivery by mist or aerosol spray or from a reservoir containing the source of peroxide are preferred. Several forms of apparatus suitable for pretreating the interior of the lumen are described in the examples and Figures below.

In a preferred method of the present invention, aqueous solutions of hydrogen peroxide can be relatively dilute, e.g., as low as 1–6% or lower by weight, since sterilization is not achieved through contact with the hydrogen peroxide solution, but rather, is achieved at low temperatures and in short periods of time upon exposure to hydrogen peroxide vapor under vacuum or vacuum combined with plasma. The apparatus and method of the present invention is particularly effective with articles having inaccessible or hard-to-reach places. The apparatus and method of the various embodiments of the present invention are especially effective in pretreating articles including long, narrow lumens, where diffusion of sterilant vapors is restricted.

Pretreating the lumen with peroxide can, in some cases, also sterilize the interior of the lumen, especially when more concentrated solutions of hydrogen peroxide are used, where the solution of peroxide is heated, or when long contact times are used. It should therefore be understood that pretreating can also comprise sterilization.

Embodiments of the invention comprise several forms of apparatus for delivering sterilant to the interior of the lumen. Several forms of apparatus for delivering sterilant to the interior of the lumen will be described and discussed in the examples and Figures below.

The apparatus may be located inside or outside of the sterilization chamber. Normally, it is preferred that the apparatus be located outside of the sterilization chamber.

The general operation of one embodiment of a preferred method of the present invention, which is useful for sterilizing the interior and preferably the exterior of articles containing lumens is as follows:

1. The interior of the lumen to be sterilized is contacted with a source of peroxide. The source of peroxide can be physically delivered as a small amount directly into the lumen, or by static soaking, liquid flow-through, mist or aerosol spray, condensation of a vapor, delivery from a reservoir, or other suitable means. The source of peroxide may optionally be heated to increase its volatility.

2. The lumen to be sterilized is placed within a chamber, and the chamber is sealed and evacuated. (The source of peroxide can also be delivered to the inside of the article after placing the lumen in the chamber.)

3. The lumen is exposed to the vacuum for a period of time and at a temperature sufficient to effect sterilization.

4. Preferably, the exterior of the article is also sterilized, simultaneously, before, or after the sterilization of the lumen. The sterilization of the exterior of the article may comprise sterilization with peroxide liquid or vapor or other suitable means including, but not limited to, plasma.

5. The sterile article with the lumen is removed from the chamber.

In yet another alternative embodiment of the present invention which pertains to all of the above methods, the article to be sterilized is exposed to a vacuum followed by low temperature plasma for a time sufficient to effect sterilization. When used in the present specification and claims, the term "plasma" is intended to include any portion of the gas or vapor that contains electrons, ions, free radicals, dissociated and/or excited atoms or molecules produced as a result of an applied electric field, including any accompanying radiation that might be produced. The applied field may cover a broad frequency range; however, a radio frequency or microwaves are commonly used.

The sterilization methods of the present invention can also be used with plasmas generated by the method disclosed in the previously mentioned U.S. Pat. No. 4,643,876. Alternatively, the methods of the present invention may be used with plasmas described in U.S. Pat. No. 5,115,166 or 5,087,418, in which the article to be sterilized is located in a chamber that is separated from the plasma source.

The present invention provides several advantages over earlier vapor sterilization systems, such as: (1) the rapid sterilization of lumened devices and diffusion restricted articles can be rapidly achieved at low temperatures; (2) relatively dilute peroxide can be used to pretreat the areas where diffusion of peroxide is restricted; (3) occluded areas due to attaching the vessel to the lumen during the sterilization process are eliminated; (4) no toxic residues remain; (5) since the product is dry at the end of the process, sterile storage of these articles can be achieved; (6) closed end lumens can be sterilized; and (7) the process can be repeated as desired without undue effects. The apparatus and method of the present invention therefore provides for a highly efficient, nonhazardous, and relatively inexpensive method of sterilization of lumens.

Other forms of diffusion restricted devices can also be sterilized with various embodiments of the methods of the present invention. For example, hinges can be sterilized by dipping in solutions comprising peroxide followed by exposure to vacuum with or without plasma.

To determine the efficacy of the preferred sterilization method of the present invention, preliminary tests were first performed to evaluate the effect of dilute hydrogen peroxide solutions on contaminated surfaces in an open, non-diffusion restricted environment. These tests are described below in Example 1.

EXAMPLE 1

To evaluate the sterilization efficacy of dilute hydrogen peroxide solution alone, a biological challenge consisting of $2.5 \times 10^6$ *Bacillus stearothennophilus* spores on a stainless steel scalpel blade was used. Inoculated blades were submerged in 40 ml of hydrogen peroxide solution in a 100 ml beaker. Four different concentrations of hydrogen peroxide solution were used: 3%, 6%, 9% and 12% by weight. The blades were allowed to soak in the peroxide solutions for various time periods. The blades were then removed from the solution and tested for sterility. The results of this testing are listed in Table 1 as a ratio of the number of inoculated blades which remain contaminated after treatment over the number of inoculated blades tested.

TABLE 1

Effect of $H_2O_2$ Concentration and Soak Times on Sporicidal Activity of $H_2O_2$ Solution

| Soak Time | Concentration of $H_2O_2$ Solution | | | |
|---|---|---|---|---|
| | 3% | 6% | 9% | 12% |
| 1 min | 4/4 | 4/4 | 4/4 | 4/4 |
| 5 min | 4/4 | 4/4 | 4/4 | 4/4 |
| 30 min | 4/4 | 4/4 | 4/4 | 4/4 |
| 60 min | 4/4 | 4/4 | 4/4 | 4/4 |

TABLE 1-continued

Effect of $H_2O_2$ Concentration and Soak Times on Sporicidal Activity of $H_2O_2$ Solution

| Soak Time | Concentration of $H_2O_2$ Solution | | | |
|---|---|---|---|---|
| | 3% | 6% | 9% | 12% |
| 90 min | N/D | 4/4 | 2/4 | 0/4 |
| 120 min | N/D | 4/4 | N/D | N/D |

*N/D = not determined

Complete sterilization was not effected until after the blades had been soaked in 12% hydrogen peroxide solution for at least 90 minutes. Moreover, none of the blades tested were sterilized after 2 hours in 6% hydrogen peroxide solution. It is clear from these data that contact with dilute hydrogen peroxide solution alone is ineffective at providing sterilization, unless extended soak times and concentrated solutions are used.

Testing was next performed to evaluate the effect on the sterilization of long, narrow lumens of a pretreatment step in which the lumens to be sterilized are exposed to hydrogen peroxide solution prior to exposure to a vacuum. The testing evaluated the efficacy of hydrogen peroxide vapor sterilization inside the lumens. The testing is detailed below in Example 2.

EXAMPLE 2

A biological challenge consisting of $1.9 \times 10^6$ *B. stearothermophilus* spores on a stainless steel scalpel blade was used. Some inoculated blades were pre-treated with a solution of aqueous hydrogen peroxide. Other inoculated blades, designated control blades, did not receive pretreatment with hydrogen peroxide. The pretreatment consisted of 5 minutes of static soaking in peroxide solution. The pre-treated blades were blotted dry, and each blade was then placed inside a stainless steel lumen, 3 mm internal diameter (ID)×50 cm length. The lumen had a center piece of 1.3 cm ID and 5 cm length. The pre-treated blade was placed inside this center piece, and additional hydrogen peroxide solution was added into the center piece in various amounts. Control blades were handled identically, except that they did not receive pretreatment with hydrogen peroxide solution. The lumens were placed in a vacuum chamber, and the chamber was evacuated to 1 Torr and held there for 15 minutes, during which time the temperature increased from approximately 23° C. to approximately 28° C. Following exposure to the vacuum, the chamber was vented and the blades were removed from the chamber and tested for sterility. The results were as follows:

TABLE 2

Effect of Pretreatment and Hydrogen Peroxide Concentration on Sterilization of the Interior of Lumens

| Additional peroxide added into the center piece | Blades not pre-treated with peroxide | Blades pre-treated in peroxide solution |
|---|---|---|
| (A) With 1% hydrogen peroxide solution and vacuum | | |
| 10 μL | + | + |
| 20 μL | + | + |
| 30 μL | + | + |

TABLE 2-continued

Effect of Pretreatment and Hydrogen Peroxide Concentration on Sterilization of the Interior of Lumens

| Additional peroxide added into the center piece | Blades not pre-treated with peroxide | Blades pre-treated in peroxide solution |
|---|---|---|
| 40 µL | + | + |
| 50 µL | + | + |
| 100 µL | + | − |
| 150 µL | + | − |
| 200 µL | − | − |
| 250 µL | − | − |
| (B) With 3% hydrogen peroxide solution and vacuum | | |
| 10 µL | − | − |
| 20 µL | − | − |
| 30 µL | − | − |
| 40 µL | − | − |
| 50 µL | − | − |
| 100 µL | − | − |
| 150 µL | − | − |
| 200 µL | − | − |
| 250 µL | − | − |
| (C) With 6% hydrogen peroxide solution and vacuum | | |
| 10 µL | − | − |
| 20 µL | − | − |
| 30 µL | − | − |
| 40 µL | − | − |
| 50 µL | − | − |

As seen from these results, sterilization can be effected using relatively dilute solutions of peroxide and exposure to negative pressure. When the vacuum was applied, the peroxide added to the center piece of the lumen was vaporized and contacted the blade, which was sufficient to effect sterilization. It can be seen from these data that the pretreatment increases effectiveness, but that pre-treatment is unnecessary as long as the peroxide diffuses from the inside to the outside.

Several forms of apparatus suitable for delivering peroxide to the interior of lumens as a pre-treatment are shown in the following Figures.

FIG. 1 illustrates one apparatus suitable for delivering peroxide to the interior of a lumen 10. A connector 12 is connected to an end 14 of the lumen. The connector contains liquid sterilant 16. In all of the Figures, the liquid sterilant preferably comprises hydrogen peroxide, peracetic acid, or mixtures thereof. The connector is attached to a pressure source 18. Optionally, the connector is also attached to a reservoir 20 which contains liquid sterilant 16. Preferably, there is a valve 22 between the reservoir 20 and the connector 12. The liquid sterilant in the reservoir is preferably, but not necessarily, the same as the liquid sterilant in the connector.

If there is liquid sterilant in the connector, the pressure from the pressure source forces the liquid sterilant in the connector into the interior of the lumen, thereby pretreating the lumen. Alternatively, or in addition, the valve 22 between the reservoir 20 and the connector can be opened, allowing liquid sterilant to enter the connector. The pressure from the pressure source drives the liquid sterilant which has entered the connector into the interior of the lumen.

Figure 2:
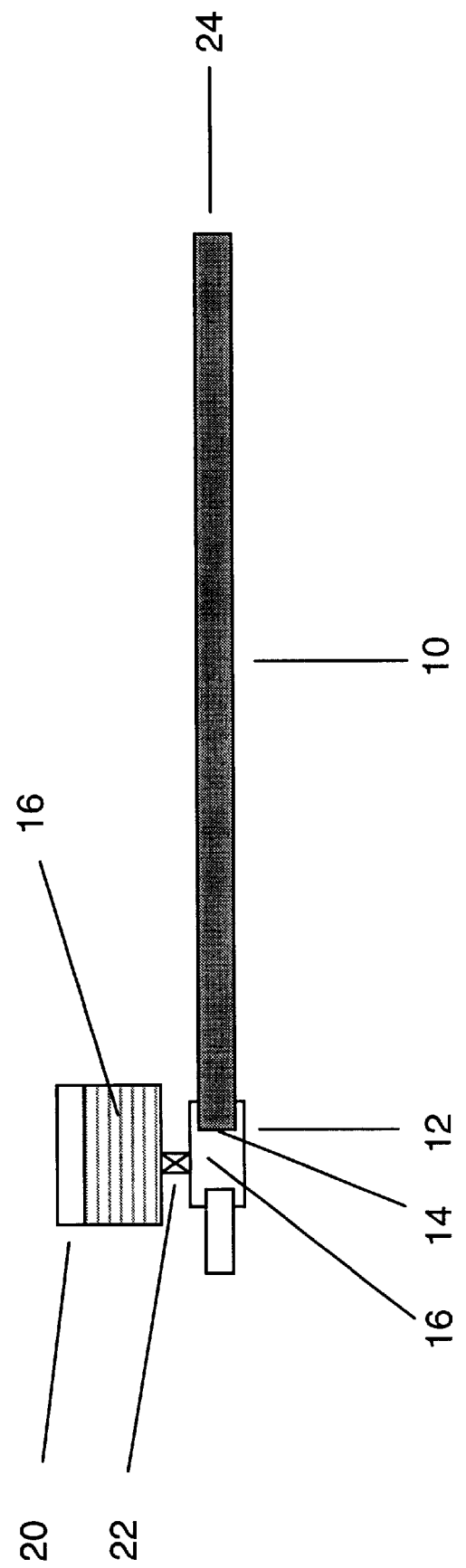
FIG. 2 is a side view of an apparatus for pretreating a lumen with a solution comprising hydrogen peroxide in which vacuum pulls the solution from a connector into the interior of the lumen.

FIG. 2 illustrates another apparatus suitable for delivering peroxide to the interior of the lumen. Because many of the components illustrated in the Figures are the same as those illustrated in FIG. 1, the same part numbers are used in the Figures when possible.

The lumen 10 is connected at end 14 to a connector 12. The connector contains a liquid sterilant 16. The connector 12 is also optionally connected to a reservoir 20 which contains liquid sterilant 16. Preferably, there is a valve 22 between the reservoir and the connector 12. The lumen is also connected to a vacuum source 24 at the end not connected to the connector.

If there is liquid sterilant in the connector 12, the vacuum from the vacuum source pulls the liquid sterilant into the interior of the lumen. Alternatively, or in addition, the valve 22 between the reservoir 20 and the connector 12 can be opened to allow liquid sterilant to flow into the connector. The vacuum from the vacuum source then pulls the liquid sterilant into the interior of the lumen, pretreating the interior of the lumen.

Figure 3:
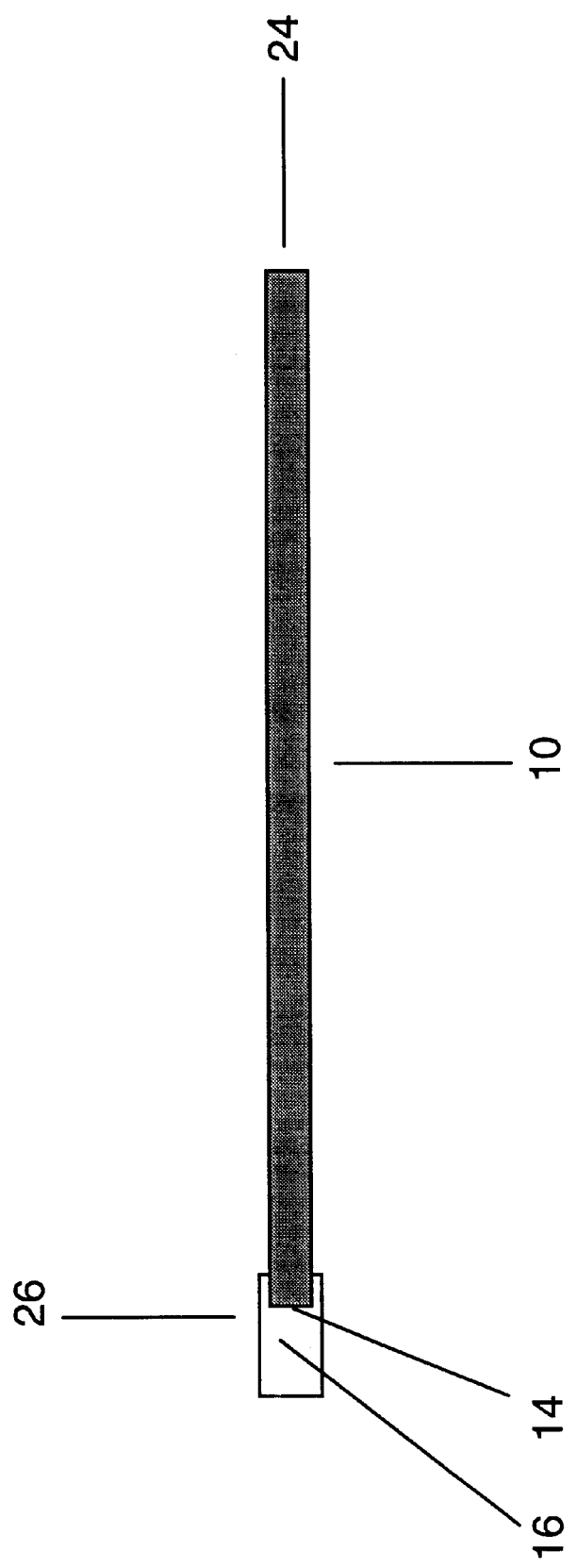
FIG. 3 is a side view of an apparatus for pretreating a lumen with a solution comprising hydrogen peroxide in which the solution is contained in a collapsible adaptor attached to an end of the lumen, and the second end of the lumen is at lower pressure than the end with the collapsible adaptor, and the collapsible adaptor collapses, forcing the solution into the interior of the lumen.

FIG. 3 shows another form of apparatus suitable for introducing liquid sterilant into the interior of a lumen 10. A collapsible adaptor 26 containing liquid sterilant is attached to an end 14 of the lumen 10. A vacuum source 24 is attached to the second end of the lumen. Alternatively, a pressure source can be placed around the collapsible adaptor.

The vacuum from the vacuum source 24 or the pressure from the pressure source causes the collapsible adaptor 26 to collapse, forcing the liquid sterilant in the collapsible adaptor to flow into the interior of the lumen, pretreating the interior of the lumen.

Figure 4:
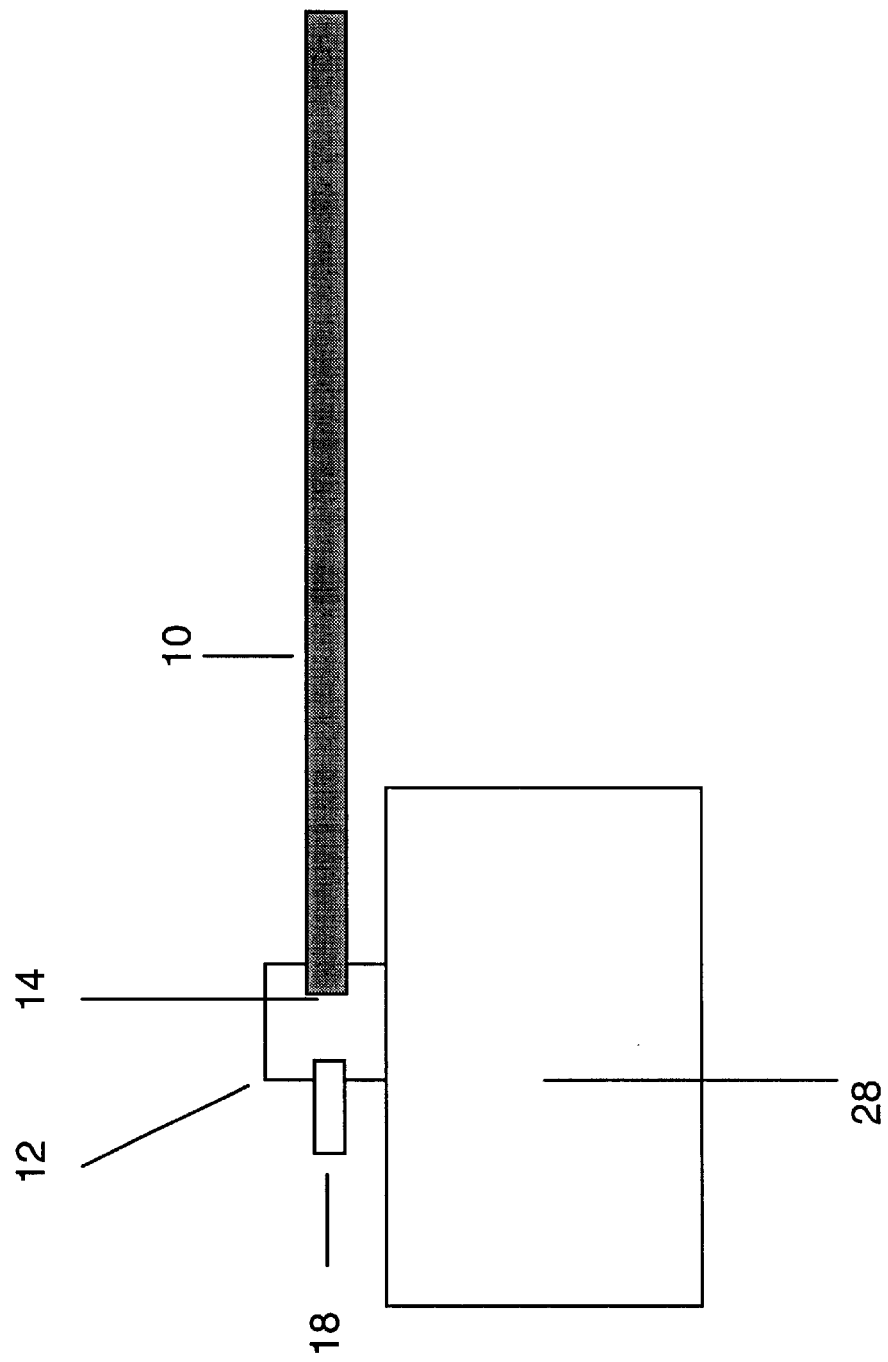
FIG. 4 is a side view of an apparatus for pretreating a lumen with a solution comprising hydrogen peroxide in which a mist or aerosol comprising hydrogen peroxide is generated and is pushed into the lumen with a pressure source.

FIG. 4 shows another form of apparatus suitable for introducing liquid sterilant into the interior of a lumen 10. A connector 12 is attached to an end 14 of the lumen 10. A generator of mist or aerosol 28 and a pressure source 18 are attached to the connector 12. The sterilant mist or aerosol preferably comprises peroxide. The peroxide preferably comprises hydrogen peroxide, peracetic acid, or mixtures thereof. More detail on several embodiments of the generator of mist or aerosol will be given later.

Regardless of which embodiment of the generator of mist or aerosol is utilized, the sterilant mist or aerosol which is generated in the source of sterilant mist or aerosol flows from the generator of mist or aerosol into the connector 12. The pressure from the pressure source 18 drives the sterilant mist or aerosol in the connector into the interior of the lumen, thereby pretreating the interior of the lumen.

Figure 5:
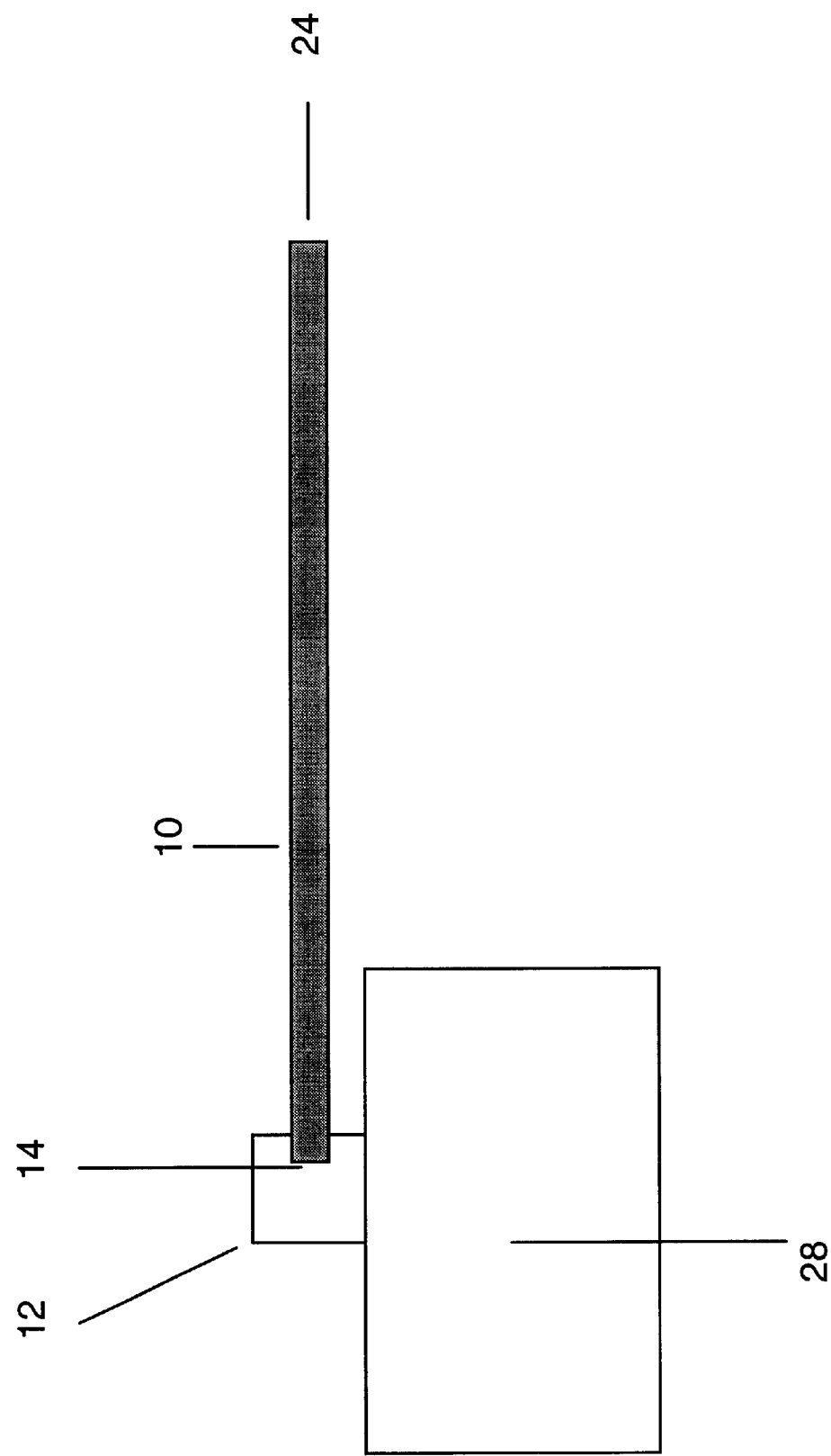
FIG. 5 is a side view of an apparatus for pretreating a lumen with a solution comprising hydrogen peroxide in which a mist or aerosol comprising hydrogen peroxide is generated and is pulled into the lumen with a vacuum source.

FIG. 5 shows another form of apparatus for introducing liquid sterilant into the interior of a lumen 10. The lumen is attached to a connector 12 at an end 14 which is connected to a generator of mist or aerosol 28. The sterilant mist or aerosol preferably comprises peroxide, even more preferably hydrogen peroxide, peracetic acid or mixtures thereof. The lumen is also connected to a vacuum source 24 by the end not attached to the connector.

The vacuum from the vacuum source 24 draws the sterilant mist or aerosol in the connector into the interior of the lumen, thereby pretreating the interior of the lumen.

Figure 6:
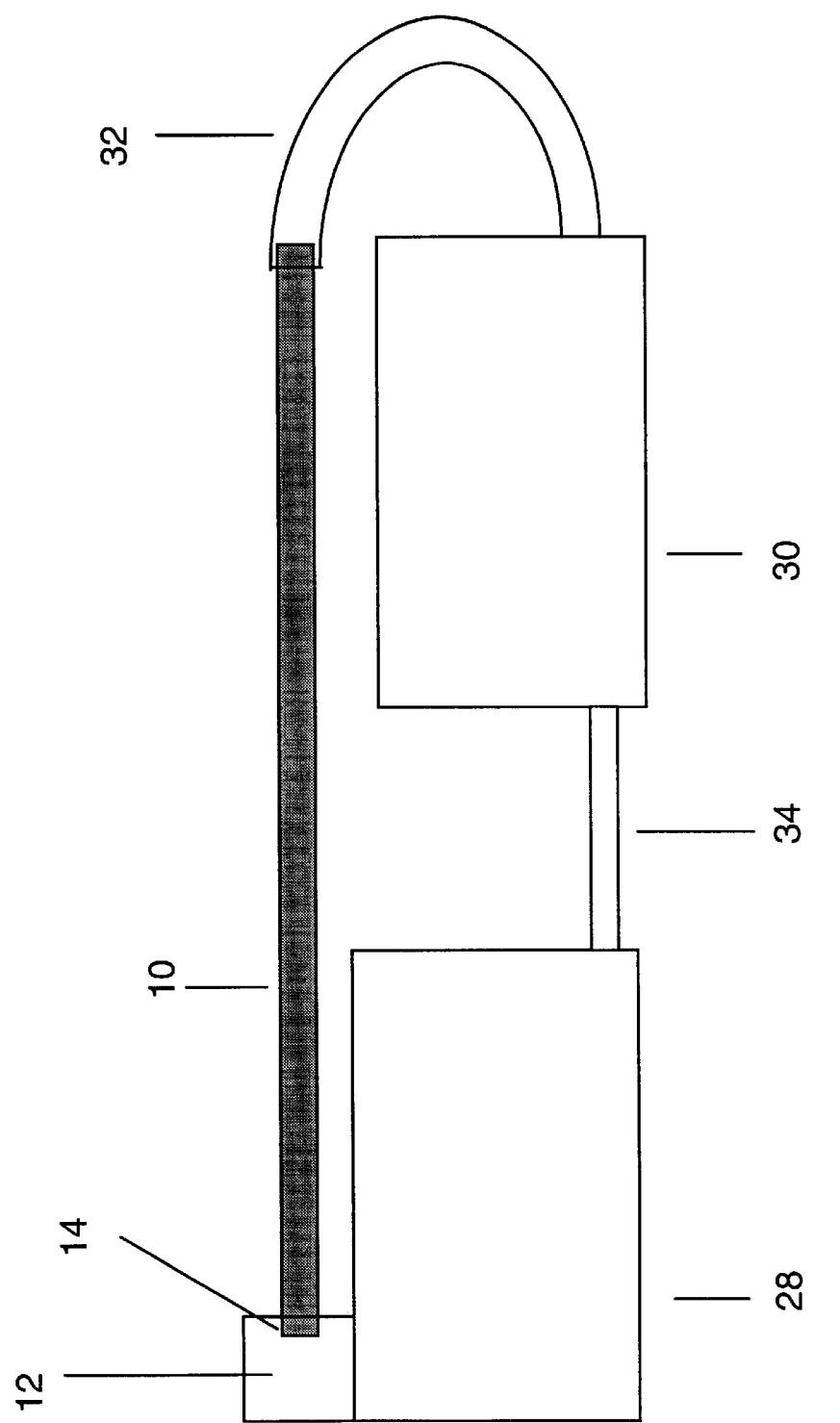
FIG. 6 is a side view of an apparatus for pretreating a lumen with a solution comprising hydrogen peroxide in which a mist or aerosol comprising hydrogen peroxide is generated, is pulled into the lumen with the vacuum from a pump, and any condensed liquid is recycled into the generator of mist or aerosol.

FIG. 6 shows another form of apparatus for introducing liquid sterilant into the interior of a lumen 10. The lumen 10 is attached at an end 14 to a connector 12 which is fluidly connected with a generator of mist or aerosol 28. In all cases, the mist or aerosol preferably comprises peroxide, even more preferably hydrogen peroxide, peracetic acid, or mixtures thereof.

The lumen 10 is also connected to a tube connector 32 at the end not attached to the connector 12. The tube connector leads to a pump 30. The pump can be either a pump which pumps liquids or a vacuum pump. If the pump is a liquid pump, it may comprise any pump which can pump liquids, including, but not limited to, peristaltic pumps, reciprocating pumps, piston pumps, ... The pump is preferably fabricated from materials which are resistant to peroxide, particularly hydrogen peroxide and peracetic acid. The pump is preferably fluidly connected to the generator of mist or aerosol 28 by a circulation pipe 34.

If the pump is a liquid pump, it may have two purposes. First, any liquid which enters the pump can be pumped back into the generator of mist or aerosol 28 through the circulation pipe 34 for reuse. Second, the suction end of the liquid pump is connected to the lumen by the tube connector 32. The vacuum generated by the pump pulls the mist or aerosol from the connector 12 into the interior of the lumen, thereby pretreating the interior of the lumen.

If no circulation pipe leading to the generator of mist or aerosol is present, the liquid pump simply serves as a source of vacuum for pulling the mist or aerosol into the interior of the lumen.

If the pump 30 is a vacuum pump, the circulation pipe 34 is not necessary. The vacuum from the vacuum pump pulls the mist or vapor from the connector 12 into the interior of the lumen, thereby introducing the liquid sterilant into the interior of the lumen, pretreating the interior of the lumen.

Figure 7:
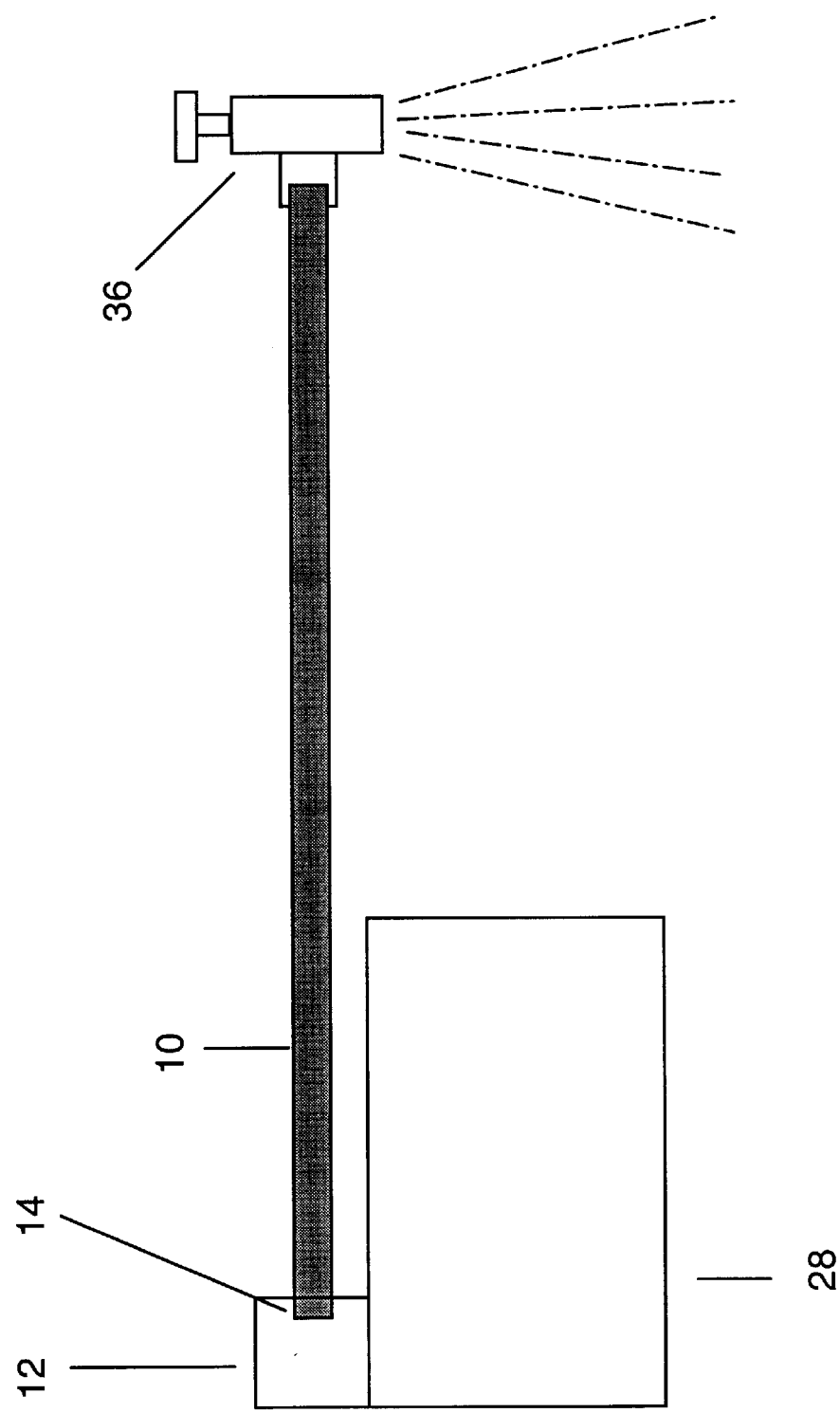
FIG. 7 is a side view of an apparatus for pretreating a lumen with a solution comprising hydrogen peroxide in which a mist or aerosol comprising hydrogen peroxide is generated and is pulled into the lumen with an aspirator.

FIG. 7 shows another form of the apparatus for introducing liquid sterilant into the interior of a lumen. A lumen 10 is attached at a first end 14 to a connector 12 which is fluidly connected to a generator of mist or aerosol 28. The lumen 10 is attached at a second end to an aspirator 36.

The aspirator 36 creates a vacuum, which pulls the mist or aerosol from the connector 12 into the interior of the lumen, thereby pretreating the interior of the lumen.

FIGS. 8–11 show more detail for various embodiments of the generator of mist or aerosol 28. In all cases, the liquid sterilant and mist or aerosol preferably comprise peroxide, even more preferably hydrogen peroxide, peracetic acid, or mixtures thereof.

Figure 8:
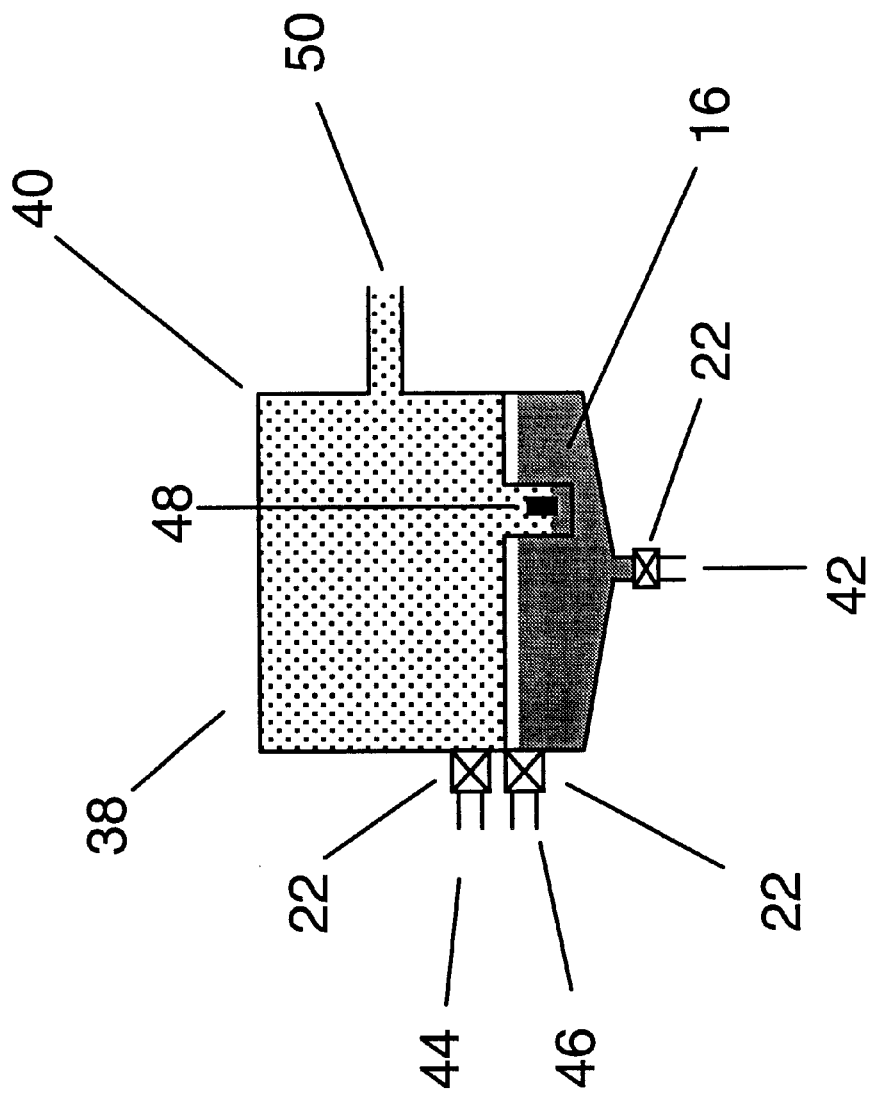
FIG. 8 is a cross sectional illustration of one embodiment of a generator of mist or aerosol, a humidifier.

FIG. 8 shows a humidifier 38. The humidifier 38 comprises a tank 40. Preferably, but not necessarily, the humidifier 38 also comprises a valve 22 leading to a drain 42. An optional compressed air pipe 44 and a liquid sterilant pipe 46 are connected to the tank 40, optionally, but preferably, through valves 22. An ultrasonic transducer 48 is located in the liquid sterilant 16 in the tank. An exit pipe 50 is fluidly connected to the connector 12, which is in turn attached to the lumen 10, as shown in FIGS. 4–7.

Liquid sterilant 16 is introduced into the tank 40 through the liquid sterilant pipe 46, and air, nitrogen or other suitable gas is introduced into the tank 40 through the compressed air pipe 44. The ultrasonic transducer 48 vibrates at high frequency and generates a mist or aerosol from the liquid sterilant. The mist or vapor is carried by the air, nitrogen, or other suitable gas through the exit pipe 50 into the interior of the lumen, thereby introducing liquid sterilant into the interior of the lumen 10. Alternatively, vacuum can be used to pull the liquid sterilant into the interior of the lumen. The liquid sterilant and mist or aerosol preferably comprise peroxide, preferably peracetic acid, hydrogen peroxide, or mixtures thereof.

Figure 9:
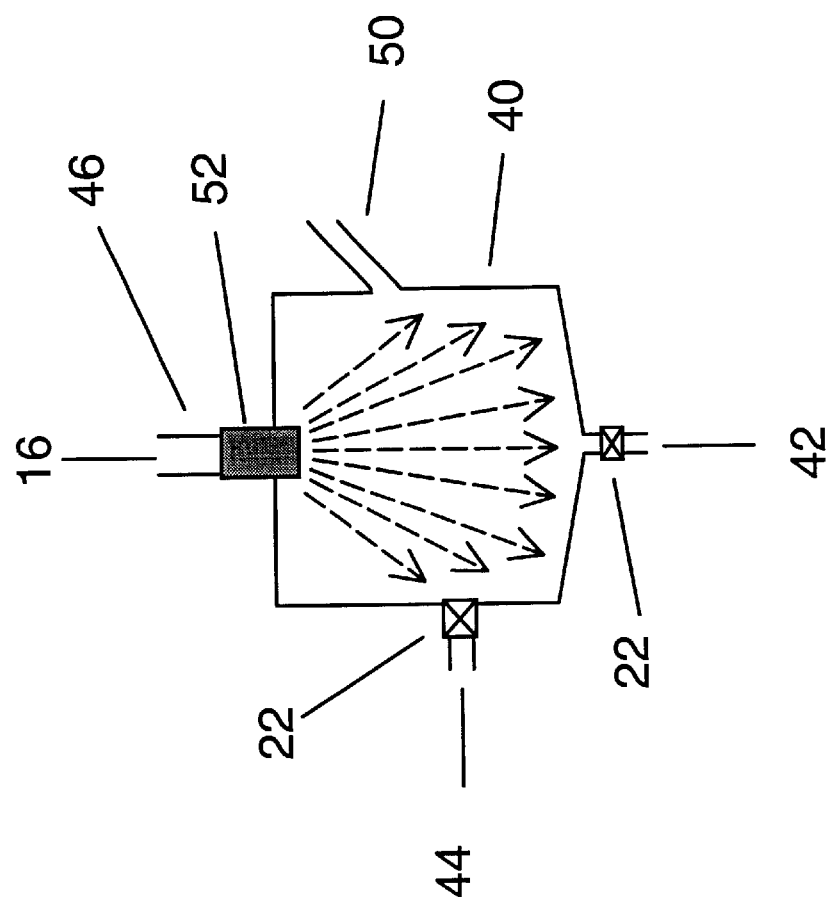
FIG. 9 is a cross sectional illustration of another embodiment of a generator of mist or aerosol, a spray with a nozzle.

FIG. 9 shows an alternative embodiment of the generator of mist or aerosol 28, a spray with nozzle. An optional compressed air pipe 44 and a solution pipe 46 are connected to a tank 40. The compressed air pipe 44 is preferably connected to the tank through a valve 22, and the solution pipe is connected to the tank through a nozzle 52. Optionally, a valve 22 at the bottom of the tank leads to a drain 42. An exit pipe 50 leads to a connector 12, which is in turn attached to the lumen 10, as shown in FIGS. 4–7.

Liquid sterilant 16 flows through the liquid sterilant pipe 46 and nozzle 52 into the tank. The nozzle forms small droplets, mist, or aerosol from the liquid sterilant. Air, nitrogen, or other suitable gas flows through the compressed air pipe 44 into the tank 40, carrying the sterilant mist or aerosol generated by the nozzle 42 into the exit pipe 50 and thereafter the lumen 10, thereby introducing liquid sterilant into the interior of the lumen, pretreating the interior of the lumen: Alternatively, vacuum can be used pull the liquid sterilant into the interior of the lumen. The liquid sterilant and mist or aerosol preferably comprise peroxide, preferably hydrogen peroxide, peracetic acid, or mixtures thereof.

Figure 10:
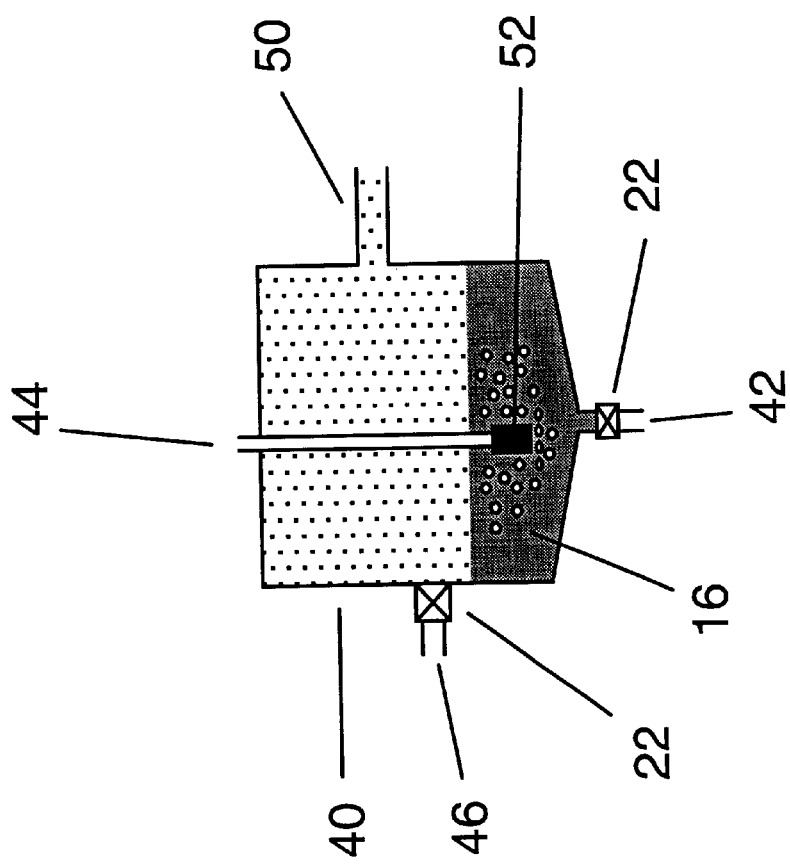
FIG. 10 is a cross sectional illustration of another embodiment of a generator of mist or aerosol in which compressed air is forced through the solution to generate the mist or aerosol.

FIG. 10 shows an alternative embodiment of the mist or aerosol generator 28. The apparatus of this embodiment comprises a tank 40, a compressed air pipe 44 entering the tank, a nozzle 52 connected to the compressed air pipe, and an exit pipe 50 which leads to the lumen 10. Optionally, there is a valve 22 leading to a drain 42. Optionally, there is also an liquid sterilant pipe 46 for introducing liquid sterilant 16 into the tank.

Liquid sterilant 16 is introduced into the tank 40, and air, nitrogen, or other suitable gas is introduced into the compressed air pipe 44 and nozzle 52. The nozzle 52 is placed in the liquid sterilant 16, so that the gas blows through the liquid sterilant, generating sterilant mist or aerosol. The mist or vapor is carried by the air, nitrogen, or other suitable gas through the exit pipe 50 into the interior of the lumen, thereby introducing liquid sterilant into the interior of the lumen 10, pretreating the interior of the lumen. Optionally, a vacuum can be used to enhance the pretreatment by pulling the mist or aerosol into the lumen. The liquid sterilant preferably comprises hydrogen peroxide, peracetic acid, or mixtures thereof.

Figure 11:
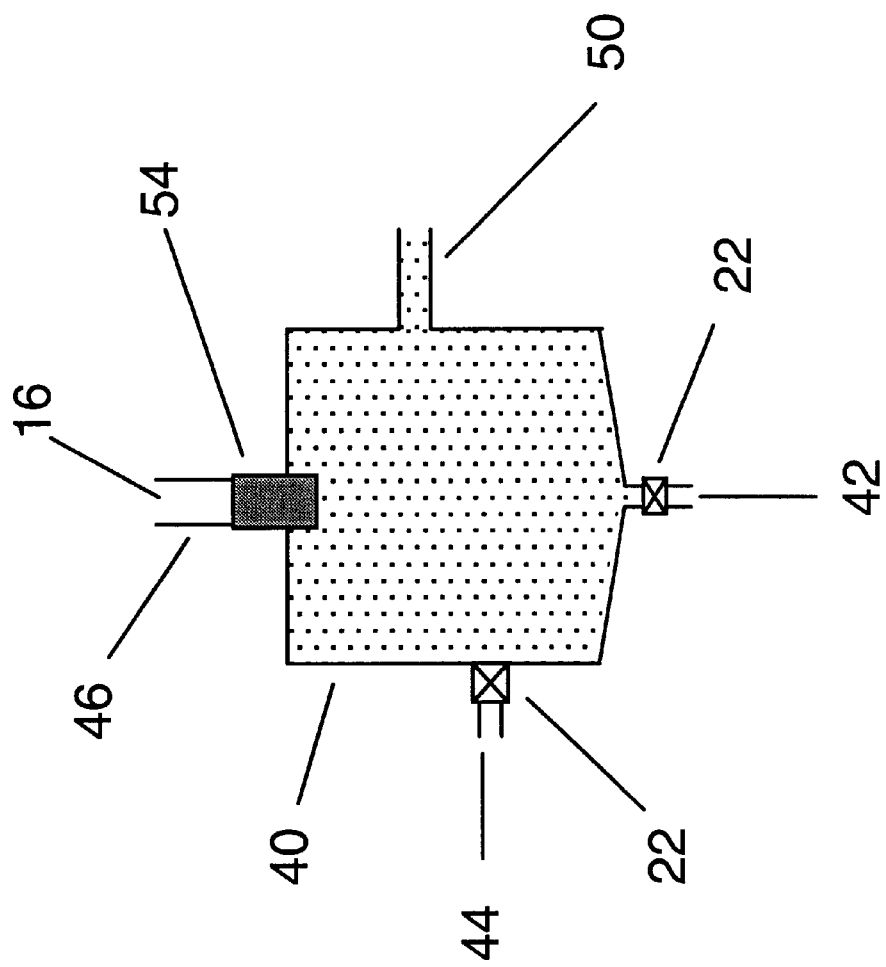
FIG. 11 is a cross sectional illustration of another embodiment of a generator of mist or aerosol, a nebulizer.

FIG. 11 shows an alternative embodiment of the mist or aerosol generator 28, a nebulizer. This embodiment of the generator of mist or aerosol comprises a tank 40, a compressed air pipe 44 entering the tank, a liquid sterilant pipe 46 leading to a nebulizer 54, and an exit pipe 50 leading to the lumen 10. Optionally, a valve 22 is attached to the compressed air pipe 44. Optionally, there is a valve 22 at the bottom of the tank leading to a drain 42.

Liquid sterilant 16 is introduced into the liquid sterilant pipe 46 and flows through the nebulizer 54 into the tank 40. The nebulizer forms a mist or aerosol from the liquid sterilant as it flows through the nebulizer. Air, nitrogen, or other suitable gas is introduced into the compressed air pipe 44 and tank 40 and carries the mist or vapor through the exit pipe 50 into the interior of the lumen, thereby pretreating the interior of the lumen 10. Optionally, a vacuum can be used to pull the mist or vapor into the interior of the lumen.

Figure 12:
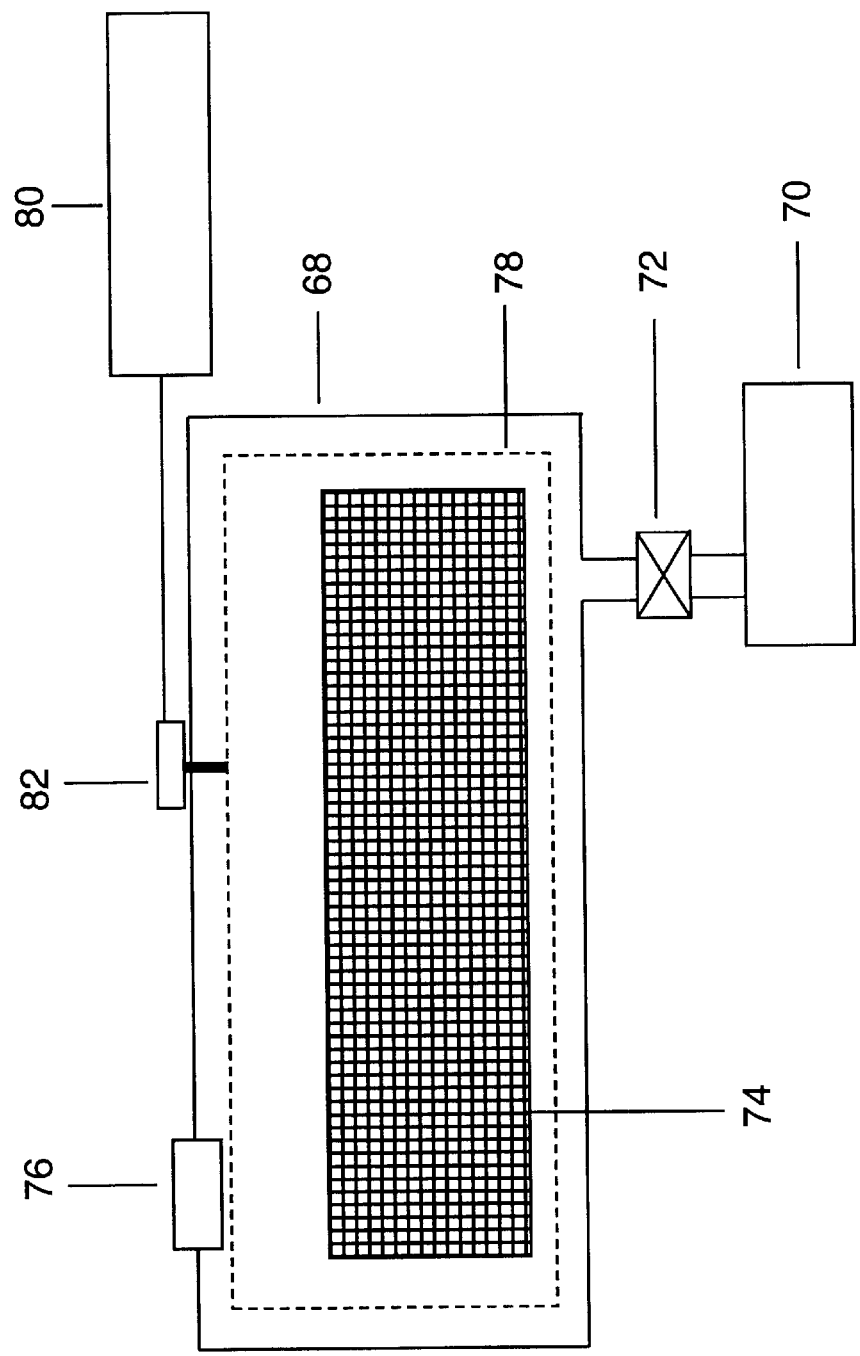
FIG. 12 is a generalized illustration of a sterilizer showing the major components.

FIG. 12 shows the configuration of a sterilizer which is suitable for sterilizing lumens with various embodiments of the method of the present invention. A vacuum chamber 68 is connected to a vacuum pump 70, preferably through a valve 72. Equipment to be sterilized is placed in a wrapped tray 74, which is placed inside of the vacuum chamber. A vaporizer 76 contains liquid sterilant, preferably hydrogen peroxide or peracetic acid. Optionally, but preferably, the vacuum chamber contains an electrode 78 connected electrically to a RF generator 80 through a matching box 82. Peroxide vapor can also be generated from a solid peroxide complex.

The vacuum pump evacuates the vacuum chamber, to a pressure below the vapor pressure of the liquid sterilant. Liquid sterilant is vaporized from the vaporizer into the interior of the chamber. Preferably, the liquid sterilant comprises hydrogen peroxide or peracetic acid. Preferably, the liquid sterilant is aqueous hydrogen peroxide with a concentration of 30 to 60% by weight. Most preferably, the liquid sterilant is 59% hydrogen peroxide. Preferably, the liquid sterilant is heated in the vaporizer before injection into the vacuum chamber. Preferably the liquid sterilant is heated to a temperature of 40 to 80° C. More preferably, the liquid sterilant is heated to a temperature of 50 to 70° C. Most preferably, the liquid sterilant is heated to approximately 60–65° C.

When electrical power is fed through the RF generator, through the matching box, and into the electrode in the evacuated vacuum chamber, a plasma is generated. Although generation of a plasma during the sterilization process is not necessary, it is preferred.

The following examples demonstrate the enhanced efficacy of sterilization of the interior of lumens by pretreatment of the interior with hydrogen peroxide, followed by exposure to a reduced pressure sterilization process. The examples also demonstrate that the exterior is effectively sterilized without the need for pretreatment.

EXAMPLE 3

Sterilization of a Flexible Endoscope with a Two-Step Process

This example demonstrates a unique two-step process for sterilizing both the interior and the exterior of a flexible endoscope. The first step involves the pretreatment of the interior with a dilute peroxide solution, and the second step is to expose the pretreated endoscope to a peroxide/plasma low pressure sterilization process. This combined process provides an easy and fast method for sterilizing the flexible endoscope.

The efficacy of the sterilization of the exterior of the flexible endoscope was demonstrated with an Olympus CF-10 colonoscope by placing five stainless steel blades inoculated with $1.8 \times 10^6$ *Bacillus stearothermophilus* spores directly on the endoscope. Three were placed on the insertion tube, and two were placed on the universal cord.

Two TEFLON lumens were used to simulate and demonstrate the efficacy of the sterilization of the interior of the flexible endoscope. The lumens were 1 mm id by 2 meters long and 3 mm id by 2 meters long. The 1 mm lumen was used to represent an air or water channel and was assembled by joining two pieces of 1 meter TEFLON lumen with a TEFLON micro tubing connector. The 3 mm lumen was used to simulate a suction channel and was constructed by joining seven sections of 3 mm lumen with latex tubing.

The assembled lumens were first simultaneously pretreated with hydrogen peroxide mist or aerosol for 30 seconds. The mist or aerosol was generated from 6% hydrogen peroxide solution in a humidifier as shown in FIG. 8, and the mist or aerosol was pulled through the lumens with a vacuum source as shown in FIG. 5. Both lumens were treated with hydrogen peroxide mist or vapor for 30 seconds, detached from the humidifier, and then treated with vacuum for 30 seconds to flow air through the lumens to remove excess peroxide from the lumens. The total pretreatment time was about 1 minute.

Three stainless steel wires inoculated with $1.7 \times 10^6$ *B. stearothermophilus* spores were then placed into each lumen after the pretreatment. For the 3 mm lumen, one wire was placed at the midpoint of the lumen, and the other two were placed about 8 cm from each end. The stainless steel wires in the 1 mm lumen were located at about the same locations as for the 3 mm lumen, except the two wires at the end were about 2 cm from the opening.

The colonoscope with five inoculated stainless steel blades and the two pretreated TEFLON lumens with a total of six inoculated stainless steel wires were placed in a CSR double-wrapped tray, which was then placed in a 75 liter sterilizer as shown in FIG. 12. A total of 1440 μLiters of 59% hydrogen peroxide was introduced into the vaporizer and was allowed to vaporize and diffuse into the chamber while the chamber was evacuated and maintained at 6 torr. Under the test conditions, the peroxide in the interior of the TEFLON lumens was also vaporized and diffused throughout the interior of the TEFLON lumens. After 2 to 5 minutes of diffusion at 6 torr, the chamber was further evacuated to 0.5 torr for exposure to plasma for 2 minutes. The results of these tests are shown in Table 3.

TABLE 3

Sterilization Tests of Pretreated Lumens with Hydrogen Peroxide/Plasma

| | Sterilization Results (# Positives/# Samples) | | |
|---|---|---|---|
| Diffusion Time at 6 Torr | Exterior of Colonoscope | Interior of 1 mm Lumen | Interior of 3 mm Lumen |
| 5 Minutes | 0/5 | 0/3 | 0/3 |
| 3 Minutes | 0/5 | 0/3 | 0/3 |
| 2 Minutes | 0/5 | 0/3 | 0/3 |

The interior of the 1 mm and 3 mm lumens were effectively sterilized by pretreatment with hydrogen peroxide mist followed by exposure to a low pressure of 6 torr for 2–5 minutes with a subsequent exposure to 2 minutes of plasma at 0.5 torr. The exterior of the colonoscope was sterilized under the same conditions but without pretreatment with hydrogen peroxide.

Pretreatment of the interior of the lumen with hydrogen peroxide mist followed by exposure to low pressure hydrogen peroxide vapor and plasma was effective in sterilizing both the interior and the exterior of the lumen.

The following example compares the sterilization results for pretreated lumens and nonpretreated lumens. The Example demonstrates that the sterilization of the interior of lumens is improved by pretreatment with hydrogen peroxide.

EXAMPLE 4

Comparison of Sterilization of Pretreated and Nonpretreated Lumens

A 1 mm id lumen and a 3 mm id lumen were pretreated with hydrogen peroxide mist as in Example 3. A second 1 mm id lumen and 3 mm id lumen were assembled but were not pretreated with hydrogen peroxide. Five inoculated blades were placed on the exterior of a colonoscope as described in Example 3.

The four simulated lumens, two pretreated and two not pretreated, and the colonoscope were placed in a tray in a sterilization chamber and were treated with hydrogen peroxide vapor and plasma as described in Example 3. The cycle conditions were 3 minutes of diffusion at 6 torr followed by 2 minutes of plasma at 0.5 torr. The results are given in Table 4.

TABLE 4

Comparison of Sterilization With and Without Hydrogen Peroxide Pretreatment

Sterilization Results (# Positives/# Samples)

|  | Exterior | Interior of 1 mm Lumen | Interior of 3 mm Lumen |
|---|---|---|---|
| With Pretreatment | 0/5 | 0/3 | 0/3 |
| Without Pretreatment |  | 3/3 | 3/3 |

The interior of the lumens which were pretreated with hydrogen peroxide were sterile after being exposed to low pressure for 3 minutes at 6 torr and 2 minutes of plasma at 0.5 torr. The interior of lumens which had not been pretreated were not sterilized under the same conditions. Pretreatment of the interior of the lumens with hydrogen peroxide greatly improved sterilization of the interior of the lumens.

Just as in Example 3, the exterior of the colonoscope was sterilized without the need for pretreatment. Pretreatment of the interior of-the lumens followed by a normal sterilization cycle with hydrogen peroxide vapor and plasma was therefore effective in sterilizing both the interior and exterior of the lumens.

The following example shows that both the interior and exterior of lumens can be sterilized by pretreatment of the interior followed by exposure to hydrogen peroxide vapor without plasma. Exposure to plasma significantly reduces the amount of time required to sterilize both the interior and the exterior, however.

EXAMPLE 5

Sterilization of Pretreated Lumens Without Plasma

The interior of 1 mm and 3 mm lumens were pretreated with hydrogen peroxide mist, and inoculated blades were placed on the exterior of a colonoscope, as previously described in Example 3.

The two pretreated lumens and the colonoscope were placed in a tray in a 75 liter sterilization chamber and were exposed to peroxide vapor generated by vaporizing 1440 µl of 59% hydrogen peroxide from the vaporizer at 6 torr for varying time periods, as shown in Table 5, followed by 2 minutes of diffusion at 0.5 torr. The conditions were thus identical as for those in Example 3, except that no plasma was introduced into the chamber, and the shortest diffusion time of 5 minutes in Table 5 without plasma was the longest time in Table 3 with plasma. The results of the test are shown in Table 5.

TABLE 5

Sterilization Tests on Pretreated Lumens With Hydrogen Peroxide Only (No Plasma Treatment)

Sterilization Results (# Positives/# Samples)

| Diffusion Time at 6 Torr | Exterior of Colonoscope | Interior of 1 mm Lumen | Interior of 3 mm Lumen |
|---|---|---|---|
| 5 Minutes | 1/5 | 1/3 | 1/3 |
| 10 Minutes | 1/5 | 0/3 | 0/3 |
| 15 Minutes | 0/5 | 0/3 | 0/3 |

A diffusion time of 5 minutes with plasma was effective in sterilizing both the exterior and interior of all of the lumens, as shown in Table 3. By contrast, as shown in Table 5, neither the interior nor the exterior of any of the lumens was sterilized with 5 minutes of diffusion at 6 torr without exposure to plasma. Exposure to plasma therefore significantly shortens the time required for sterilization of both the interior and the exterior of the lumens.

After 10 minutes of diffusion at 6 torr, the interior of both lumens were sterilized. There was still one blade on the exterior which was not sterile. After 15 minutes of diffusion, both the exterior and the interiors were sterile. By contrast, only 2 minutes of diffusion followed by plasma was effective in sterilizing both the interior and the exterior of the lumens, as shown in Table 3. Exposure to plasma clearly reduces the sterilization times required for both the interior and the exterior of the lumens.

In general, this enhanced sterilization process involves two steps to sterilize the lumen device. The first step is to pretreat the interior of the lumen device with a liquid comprising hydrogen peroxide, and the second step is to expose the pretreated device to a reduced pressure sterilization process. The reduced pressure sterilization process vaporizes the peroxide in the lumen and sterilizes the interior and exterior of the lumen device. Preferably, the reduced pressure sterilization process comprises hydrogen peroxide vapor and optionally comprises plasma. This two-step sterilization process provides an easy and fast method for sterilizing a lumen device. It also eliminates any potential occluded area created by attaching a vessel to the lumen device during the sterilization process.

This sterilization method also creates a method for concentrating the liquid peroxide in the vaporizer for sterilization. Water is lighter and has a lower boiling point than hydrogen peroxide. When water and hydrogen peroxide vaporize from the vaporizer and diffuse into the sterilizer, water vaporizes faster and diffuses more quickly than the hydrogen peroxide. Therefore, hydrogen peroxide can easily be concentrated in the vaporizer by controlling the vaporization rate from the vaporizer. Also, by not closing the valve between the sterilizer and pump during the process, more water than hydrogen peroxide can be removed from the sterilizer. Compared to the normal vapor phase sterilization process, where the sterilizer is evacuated and the valve is closed before the vapor sterilant is introduced into the sterilizer, this process adds another benefit which enhances the overall sterilization process.

Conclusions

Pretreatment of the interior of the lumens with hydrogen peroxide followed by exposure to low pressures has been shown to significantly improve the sterilization of the interior of lumens. Subsequent exposure to plasma significantly reduces the time required for sterilization, compared to that required for hydrogen peroxide alone.

Although the exterior of the lumen can be sterilized by exposure to hydrogen peroxide vapor alone, the time required for sterilization of the exterior can be significantly reduced by exposure to plasma.

Pretreatment of the interior of the lumen with liquid hydrogen peroxide together with exposure of the exterior of the lumen to hydrogen peroxide vapor has been shown to effective in sterilizing both the exterior and the interior of the lumen. Exposure to plasma significantly reduces sterilization times for both the interior and exterior of the lumens.

While embodiments and applications of this invention have been shown and described, it should be apparent to those skilled in the art that many more modifications are possible without departing from the scope of the invention. The invention is therefore not to be restricted, except in the spirit of the appended claims.

What is claimed is:

1. A method for pretreating a lumen with liquid comprising hydrogen peroxide, said lumen having a first end, a second end, and an interior, comprising, attaching the first end of said lumen to a connector;

delivering said liquid comprising hydrogen peroxide from a source of said liquid comprising hydrogen peroxide to said connector;

delivering said liquid comprising hydrogen peroxide from said connector to said lumen;

wherein said delivering of said liquid comprising hydrogen peroxide from said connector to said lumen is performed by creating a pressure difference between a first pressure at the connector and a second pressure at the second end of said lumen, wherein both said first pressure and said second pressure are above the vapor pressure of the liquid comprising hydrogen peroxide, and wherein the second end of said lumen is at a lower pressure than the connector, thereby causing the liquid comprising hydrogen peroxide to flow through said lumen; and vaporizing at least a portion of said liquid comprising hydrogen peroxide.

2. The method of claim 1, wherein said connector is attached to a receptacle containing a liquid comprising hydrogen peroxide.

3. The method of claim 1, wherein said connector is collapsible.

4. The method of claim 1, wherein said liquid comprising hydrogen peroxide is a mist or aerosol.

5. The method of claim 1, further comprising sterilizing said lumen.

6. An apparatus for pretreating a lumen, said lumen having two ends and an interior, comprising a connector containing liquid hydrogen peroxide, wherein said connector is attached to a first end of said lumen and said liquid hydrogen peroxide is in the form of a mist or aerosol;

means for creating a pressure difference between the connector and a second end of said lumen, wherein the second end of said lumen is at a lower pressure than the connector, thereby causing the liquid hydrogen peroxide to flow through said lumen; and a generator of mist or aerosol, wherein said generator is attached to said connector in a manner allowing said mist or aerosol to enter said connector.

7. The apparatus of claim 6, wherein said generator comprises a humidifier.

8. The apparatus of claim 7, wherein said humidifier comprises an ultrasonic transducer.

9. The apparatus of claim 6, wherein said generator comprises a liquid spray nozzle.

10. The apparatus of claim 6, wherein said generator comprises:

a tank containing a liquid comprising hydrogen peroxide; and a gas nozzle, wherein the gas nozzle is situated at least partially in said liquid.

11. The apparatus of claim 6, wherein said generator comprises a nebulizer.

12. The apparatus of claim 6, wherein the means for creating a pressure difference is a source of vacuum.

13. The apparatus of claim 6, additionally comprising:

a vacuum chamber capable of vaporizing hydrogen peroxide; and a source of sterilant located in an enclosure, wherein said enclosure is in fluid communication with the chamber and is able to introduce sterilant into the interior of said chamber.

14. The apparatus of claim 13, wherein said sterilant comprises hydrogen peroxide.

15. The apparatus of claim 13, additionally comprising a source of plasma.

16. A method of pretreating and sterilizing the interior and exterior of a lumen, comprising:

contacting the interior of said lumen with a liquid comprising hydrogen peroxide, wherein said liquid is delivered from a source of liquid;

placing said lumen in a chamber, wherein said placing occurs before or after contacting:

removing said source of liquid from the lumen;

evacuating said chamber, wherein the removing occurs before evacuating;

introducing sterilant into said chamber from an enclosure in fluid communication with the chamber;

vaporizing said liquid in the interior of the lumen; and sterilizing the interior and exterior of the lumen.

17. The method of claim 16, wherein said contacting step comprises delivery via one or more methods selected from the group consisting of direct delivery, injection, static soak, liquid flow-through, aerosol or mist, condensation, and physical placement.

18. The method of claim 16, further comprising exposing said lumen to a plasma.

19. The method of claim 18, wherein said method is performed within a first chamber and wherein said plasma is generated in a second, separate chamber and said method further comprises the step of flowing said plasma into said first chamber.

20. The method of claim 18, wherein said plasma is generated in the chamber.

21. The method of claim 16, wherein said sterilant comprises hydrogen peroxide.

22. The method of claim 16, wherein said lumen has two ends and wherein said contacting comprises:

attaching a collapsible container containing a liquid comprising hydrogen peroxide to a first end of said lumen; and generating a pressure difference between said collapsible container and a second end of said lumen, wherein said second end is at lower pressure than said collapsible container, thereby collapsing said collapsible container and contacting said liquid comprising hydrogen peroxide with the interior of said lumen.

23. The method of claim 16, wherein said lumen has at least two ends and wherein contacting comprises:

attaching a container containing a liquid comprising hydrogen peroxide to a first end of said lumen; and generating a pressure difference between the container and a second end of said lumen, wherein said second end is at lower pressure than said container, thereby contacting said liquid with the interior of said lumen.

24. The method of claim 16, wherein said lumen has two ends and wherein said contacting comprises:

generating a mist or aerosol comprising hydrogen peroxide;

flowing said mist or aerosol into an connector attached to a first end of said lumen; and generating a pressure difference between said connector and a second end of said lumen, wherein said second end is at lower pressure than said connector, thereby contacting said mist or aerosol with the interior of said lumen.

25. The method of claim 16, wherein the sterilant is introduced into the chamber before or during said vaporizing of the liquid.

26. The method of claim 16, wherein the introduction of the sterilant concentrates said sterilant in said enclosure.

27. The method of claim 16, wherein said sterilant is generated from a source of sterilant.

28. The method of claim 27, wherein said source of sterilant comprises liquid peroxide or a solid peroxide complex.

29. The method of claim 27, wherein the source of sterilant is introduced into the enclosure before or during the evacuating step.

* * * * *